United States Patent [19]

Jarvi et al.

[11] Patent Number: 5,064,864

[45] Date of Patent: Nov. 12, 1991

[54] DI- AND TETRA-FLUORO ANALOGS OF SQUALENE AS INHIBITORS OF SQUALENE EPOXIDASE

[75] Inventors: Esa T. Jarvi; Michael L. Edwards, both of Cincinnati; James R. McCarthy, West Chester, all of Ohio

[73] Assignee: Merrell Dow Pharmaceuticals Inc., Cincinnati, Ohio

[21] Appl. No.: 626,507

[22] Filed: Dec. 12, 1990

Related U.S. Application Data

[62] Division of Ser. No. 502,203, Mar. 30, 1990, Pat. No. 5,011,859.

[51] Int. Cl.$^5$ .................... C07C 17/26; C07C 21/18; A61K 31/35
[52] U.S. Cl. .................... 514/739; 514/746; 568/843; 570/136
[58] Field of Search ........... 570/136; 568/843; 514/739, 746

[56] References Cited

U.S. PATENT DOCUMENTS

| | | | |
|---|---|---|---|
| 3,876,672 | 4/1975 | Meowca | 568/882 |
| 4,278,819 | 7/1981 | Korff et al. | 568/882 |
| 4,455,441 | 6/1984 | Prestwich | 568/843 |
| 4,839,390 | 6/1989 | Naumann et al. | 570/136 |
| 4,876,295 | 10/1989 | Peake | 514/746 |

OTHER PUBLICATIONS

Sen et al., "J. Med. Chem." 32 (1989) pp. 2152-2158.
Cervt et al., "Eur. J. Med. Chem." 22 (1987) pp. 199-208.
Hayashi et al., "Chemistry Letters", Chemical Society of Japan (1979) pp. 983-986.

Primary Examiner—J. E. Evans
Attorney, Agent, or Firm—Louis J. Wille

[57] ABSTRACT

This invention relates to certain novel di- and tetrafluoro analogs of squalene and to their methods of use in lowering plasma cholesterol and in inhibiting squalene epoxidase in patients in need thereof.

6 Claims, No Drawings

DI- AND TETRA-FLUORO ANALOGS OF SQUALENE AS INHIBITORS OF SQUALENE EPOXIDASE

CROSS-REFERENCE TO RELATED APPLICATION

This is a division of application Ser. No. 07/502,203 filed Mar. 30, 1990, now U.S. Pat. No. 5,011,859.

BACKGROUND OF THE INVENTION

The present invention relates to certain novel di- and tetra-fluoro analogs of squalene which are useful as inhibitors of squalene epoxidase and as agents which lower total serum cholesterol in patients in need thereof. The present invention also provides pharmaceutical compositions for the use of these novel compounds as well as a novel process for their synthesis.

The conversion of the acyclic polyolefin squalene to the cyclic steroid lanosterol is a key step in the biogenesis of cholesterol. This conversion occurs in two steps. Squalene epoxidase catalyzes the conversion of squalene to (3S)-2,3-oxidosqualene. Oxidosqualene cyclase then converts (3S)-2,3-oxidosqualene to lanosterol. Lanosterol is converted through a number of subsequent enzymatic steps to cholesterol. Inhibition of squalene epoxidase decreases the amount of oxidosqualene available for conversion to cholesterol. Inhibition of squalene epoxidase thus results in a decrease in the amount of cholesterol synthesized and ultimately causes a lowering of cholesterol in the blood.

Sen and Prestwich [J. Med. Chem. 1989, 32, 2152–2158] have synthesized a variety of squalene analogs in an attempt to produce an effective inhibitor of squalene epoxidase.

Included in the compounds synthesized and tested for squalene epoxidase activity were the 1,1-di- and 1,1,22,22-tetra-bromo- and 1,1-di- and 1,1,22,22-tetrachloro analogs of squalene. These compounds, unlike the di- and tetra-fluoro analogs of the present invention, were found to have no or very poor inhibitory effect on squalene epoxidase. Surprisingly, the di- and tetra-fluoro analogs of the present invention are very effective inhibitors of squalene epoxidase.

Atherosclerosis as manifested in its major clinical complication, ischaemic heart disease, continues to be a major cause of death in industrialized countries. It is now well accepted that atherosclerosis can begin with local injury to the arterial endothelium followed by proliferation of arterial smooth muscle cells from the medial layer to the intimal layer along with deposition of lipid and accumulation of foam cells in the lesion. As the atherosclerotic plaque develops it progressively occludes more and more of the affected blood vessel and can eventually lead to ischaemia or infarction. Therefore, it is desirable to provide methods of inhibiting the progression of atherosclerosis in patients in need thereof.

There is now a large body of evidence demonstrating that hypercholesterolemia is an important risk factor associated with heart disease. For example, in December 1984, a National Institute of Health Consensus Development Conference Panel concluded that lowering definitely elevated blood cholesterol levels (specifically blood levels of low-density lipoprotein cholesterol) will reduce the risk of heart attacks due to coronary heart disease. Accordingly, it is desirable to provide a method for reducing blood cholesterol in patients with hypercholesterolemia.

Typically, cholesterol is carried in the blood of warm-blooded animals in certain lipid-protein complexes such as chylomicrons, very low density lipoprotein (VLDL), low density lipoprotein (LDL), and high density lipoprotein (HDL). It is widely accepted that LDL functions in a way that directly results in deposition of the LDL cholesterol in the blood-vessel wall and that HDL functions in a way that results in the HDL picking up cholesterol from the vessel wall and transporting it to the liver where it is metabolized [Brown and Goldstein, Ann. Rev. Biochem. 52, 223 (1983); Miller, Ann. Rev. Med. 31, 97 (1980)]. For example, in various epidemiologic studies the LDL cholesterol levels correlate well with the risk of coronary heart disease whereas the HDL cholesterol levels are inversely associated with coronary heart disease [Patton et al., Clin. Chem. 29, 1890 (1983)]. It is generally accepted by those skilled in the art that reduction of abnormally high LDL cholesterol levels is effective therapy not only in the treatment of hypercholesterolemia but also in the treatment of atherosclerosis.

The novel di- and tertra-fluoro squalene analogs of the present invention are inhibitors of squalene epoxidase. These compounds are thus useful in lowering blood cholesterol in patients in need thereof.

SUMMARY OF THE INVENTION

The present invention provides novel di- and tertra-fluoro squalene analogs of formula I

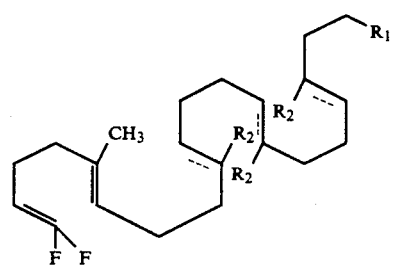

wherein
  each dotted line individually represents an optional double bond,
  $R_1$ is —CH=CF$_2$, —CH=CR$_3$R$_4$ or —R$_5$—OH, wherein R$_3$ and R$_4$ are each independently a C$_1$-C$_4$ alkyl, and R$_5$ is a C$_1$-C$_4$ alkylene, and
  each R$_2$ is independently hydrogen or methyl.

The present invention also provides novel di- and tertra-fluoro squalene analogs of formula II

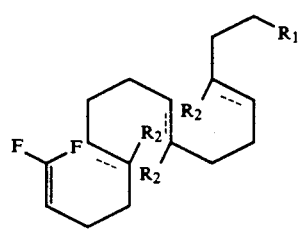

wherein
  each dotted line individually represents an optional double bond, $R_1$ is —CH=CF$_2$, —CH=CR$_3$R$_4$ or —R$_5$—OH, wherein R$_3$ and R$_4$ are each independently a C$_1$-C$_4$ alkyl, and R$_5$ is a C$_1$-C$_4$ alkylene, and each R$_2$ is independently hydrogen or methyl.

The present invention also provides novel di- and tetra-fluoro squalene analogs of formula III

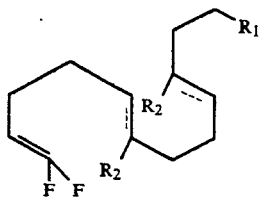

(III)

wherein each dotted line individually represents an optional double bond, $R_1$ is —CH=CF$_2$, —CH=CR$_3$R$_4$ or —R$_5$—OH, wherein R$_3$ and R$_4$ are each independently a C$_1$-C$_4$ alkyl, and R$_5$ is a C$_1$-C$_4$ alkylene, and each R$_2$ is independently hydrogen or methyl.

The present invention further provides a method of inhibiting squalene epoxidase in a patient in need thereof comprising administering to said patient an effective squalene epoxidase inhibitory amount of a compound of formula I, II or III.

The present invention also provides a method of lowering plasma cholesterol in a patient in need thereof comprising administering to said patient an effective hypocholesterolemic amount of a compound of formula I, II or III.

Finally, the present invention provides a novel chemical intermediate of formula IV

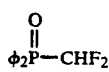

IV wherein φ is phenyl. This chemical intermediate is useful in the synthesis of compounds of the formula I, II and III.

DETAILED DESCRIPTION OF THE INVENTION

The structure presented for the compounds of formulae I, II and III represent novel di- and tetra-fluoro analogs of squalene. The dotted lines depicted in these formulae each individually represent an optional double bond.

As used herein, the term "R$_1$" refers to a monovalent radical of the formula —CH=CF$_2$, —CH=CR$_3$R$_4$ or —R$_5$—OH, wherein R$_3$ and R$_4$ are each independently a C$_1$-C$_4$ alkyl and R$_5$ is a C$_1$-C$_4$ alkylene. Specifically included within the scope of R$_1$ are —CH=CF$_2$, —CH=C(CH$_3$)$_2$ and —CH$_2$CH$_2$—OH.

The terms "R$_3$" and "R$_4$" each independently refer to a saturated alkyl of from 1 to 4 carbon atoms of straight or branched chain configuration, including methyl, ethyl, propyl, isopropyl, butyl, isobutyl, tertiary butyl and the like.

The term "R$_5$" refers to a saturated alkylene of from 1 to 4 carbon atoms of straight or branched chain configuration, including —CH$_2$—, —CH$_2$CH$_2$—, —CH$_2$CH$_2$CH$_2$—, —CH(CH$_3$)CH$_2$—, —CH(CH$_3$)—, —C(CH$_3$)$_2$—, —CH$_2$CH$_2$CH$_2$CH$_2$—, —CH$_2$CH(CH$_3$)$_2$— and the like.

The di- and tetra-fluoro squalene analogs of formula I can be prepared according to the general synthetic procedure as set forth in Scheme A wherein all terms are as previously defined and the term "R'$_1$" is —C(O)H, —CH=CR$_3$R$_4$ or —R$_5$—OH.

SCHEME A

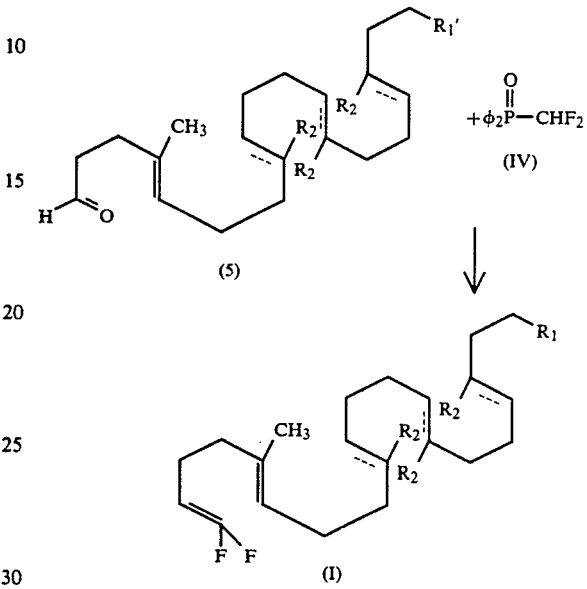

The appropriate aldehyde (5) is reacted with difluoromethyl-diphenyl-phosphine oxide (IV) in the presence of base to form the compound of formula (I). Although a variety of bases can be used, those bases which are derived from butyl-lithium and a secondary amine are particularly useful in this process. Lithium diisopropylamide and lithium bis(trimethylsilyl)amide are preferred bases for this process. This reaction can be carried out initially at temperatures from about −78° C. to about −20° C., followed by reflux at about 65° C. Ordinarily, this reaction will conveniently be carried out in an inert solvent such as tetrahydrofuran. Generally, the aldehyde (5) will be added to a mixture of difluoromethyl-diphenyl-phosphine oxide (IV) and base in an inert solvent.

Where a difluoro squalene analog is desired as the compound of formula (I), the appropriate aldehyde will be a monoaldehyde, such as (E,E,E,E)-4,8,13,17,21-pentamethyl-4,8,12,16,20-docosapentaenal. Where a tetra-fluoro squalene analog is to be prepared, the appropriate aldehyde (5) will be a dialdehyde, such as (E,E,E,E)-4,8,13,17-tetramethyl-4,8,12,16-icosatetraendial.

Difluoromethyl-diphenyl-phosphine oxide (IV) can be prepared by reacting diphenylphosphine oxide with chlorodifluoromethane in the presence of a base such as butyl-lithium, potassium hydride, lithium diisopropylamide or lithium bis(trimethylsilyl)amide. Butyl lithium is preferred as the base in this reaction.

The di- and tetra-fluoro squalene analogs of formulae II and III can also be prepared according to the procedures outlined in Scheme A by utilizing the appropriate aldehyde as the starting material.

Aldehydes which are useful in the synthesis of the compounds of formulae I, II and III are readily available or can be prepared according to conventional procedures and techniques which are well known and appreciated in the art. For example, (E,E,E,E)-

4,8,13,17,21-pentamethyl-4,8,12,16,20-docosapentaenal and (E,E,E,E)-4,8,13,17-tetramethyl-4,8,12,16-icosatetraendial can be prepared according to the procedure of Ceruti et al. [*Eur. J. Med. Chem.* 1987, 22, 199–208]. This procedure is described in Scheme B wherein all terms are as previously defined and R''$_1$ is —CH=CR$_3$R$_4$ or —R$_5$—OH; R'''$_1$ is —C(Br)—C(OH)(CH$_3$)$_2$, —CH=CR$_3$R$_4$ or —R$_5$—OH; and R''''$_1$ is

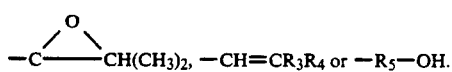
—C——CH(CH$_3$)$_2$, —CH=CR$_3$R$_4$ or —R$_5$—OH.

SCHEME B

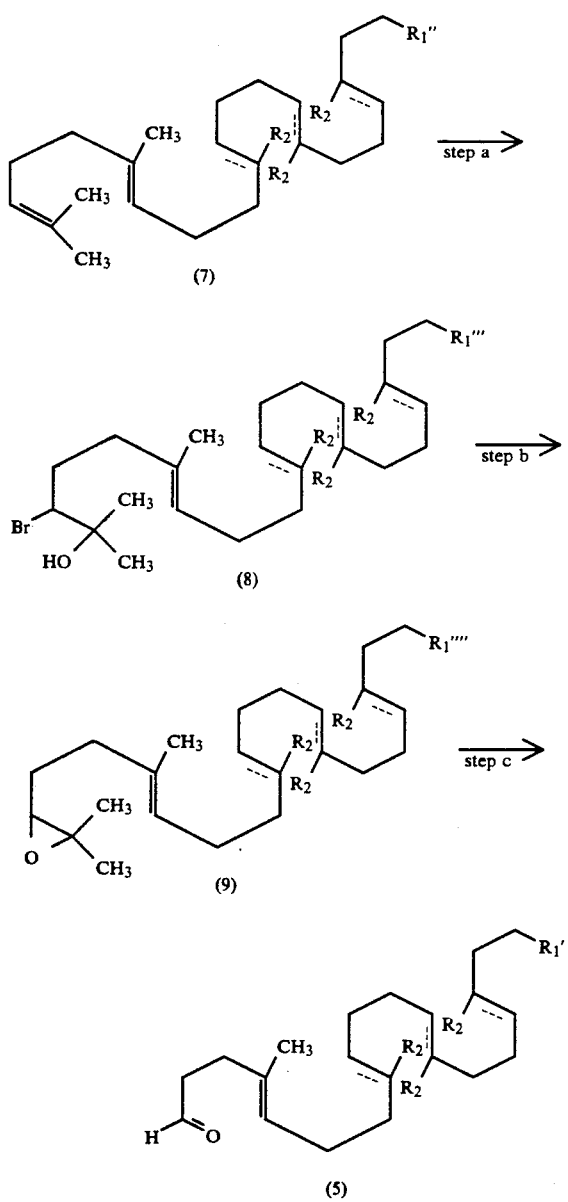

In step a, hypobromous acid is added to one or both terminal double bonds of squalene or its analog (7) to allow the formation of the corresponding terminal mono- or di-bromohydrin (8). Squalene or its analog (7) is treated with a reagent such as aqueous N-bromosuccinimide. Where a mono-aldehyde is desired, one equivalent of the N-bromosuccinimide is used. Where a di-aldehyde is desired, two equivalents of the N-bromosuccinimide is used.

In step b, the mono or di-bromohydrin derivative (8) is converted to the corresponding mono- or di-epoxide (9) by treatment with a base such as potassium carbonate.

In step c, the mono- or di-epoxide (9) is then converted to the corresponding mono- or di-aldehyde (5) by oxidation with periodic acid in diethyl ether.

By adding hypobromous acid to squalene or its analog (7), double bonds other than the terminal double bonds can be attacked by the reagent. Where non-terminal double bonds are subjected to this addition, debromination and oxidation results in the formation of an aldehyde which can be utilized in the synthesis of compounds of formulae II and III.

Alternatively, compounds of formulae I, II, and III can be prepared by the method of Hayashi et al., *Chemistry Letters*, Chemical Society of Japan, 983–86, 1979, by reacting the appropriate aldehyde in situ with dibromodifluoromethane and triphenylphosphine in the presence of zinc dust.

The following examples present typical syntheses as described above. The examples are understood to be illustrative only and are not intended to limit the scope of the invention in any way. As used in the following examples, the following terms have the meanings indicated: "g" refers to grams, "mmol" refers to millimoles, "mL" refers to milliliters, "M" refers to molar, "° C." refers to degrees Celsius, "TLC" refers to thin layer chromatography, "mg" refers to milligrams, "THF" refers to tetrahydrofuran.

EXAMPLE 1

Difluoromethyl-diphenyl-phosphine oxide

Cool a mixture of 4.96 g (24.5 mmol) of diphenylphosphine oxide in 100 mL of dry THF in a dry-ice/isopropanol bath. To this mixture add 16.0 mL (25.6 mmol) of 1.6M n-butyl-lithium in hexane and stir the cooled mixture for 30 minutes. Condense 4 mL of chlorodifluoromethane into the reaction using a dry-ice condenser and stir in the cooling bath for 2 hours. Remove from the cooling bath and stir the reaction mixture overnight under a dry-ice condenser such that the chlorodifluoromethane refluxes as the reaction is left.

Evaporate the bulk of the THF in vacuo and partition the residue between 300 mL of dichloromethane and water. Dry the dichloromethane layer with anhydrous MgSO$_4$ and evaporate in vacuo to yield 4.61 g (74% yield) of the title compound as an oil which solidifies upon standing. Recrystallize in hexane/dichloromethane to yield needles, mp. 93°–94° C. Analysis by TLC (silica gel, eluting with ethyl acetate) indicates the title compound with an R$_f$ of 0.64.

$^1$H-NMR (CDCl$_3$): δ6.357 (1H, td, J=49.1, 22.3), 7.5–7.92 (10H, m).

$^{19}$F-NMR (δ from CFCl$_3$, CDCl$_3$): −132.64 (dd, J=69.7, 49.4 Hz).

EXAMPLE 2

(E,E,E,E)-1,1-Difluoro-5,9,14,18,22-pentamethyl-1,5,9,13,17,21-tricosahexaene

Prepare lithium diisopropylamide at 0° C. from 0.98 mL of 1.48M n-butyl-lithium in hexane (1.32 mmol), 0.20 mL of diisopropylamine and 3 mL of dry THF.

Cool the mixture in a dry-ice/isopropanol bath and add dropwise difluoromethyl-diphenyl-phosphine oxide (300 mg, 1.2 mmol) in 1.5 mL THF. Rinse the flask with 0.5 mL of THF two times adding the rinse to the reaction. Allow the mixture to stir for 15 minutes. Add dropwise (E,E,E,E)-4,8,13,17,21-pentamethyl-4,8,12,16,20-docosapentaenal (prepared as described by Ceruti et al., *Eur. J. Med. Chem.* 1987, 22, 199–208) in 1 mL THF. Rinse the flask with 0.5 mL of THF adding the rinse to the reaction. Stir the reaction mixture for 1 hour in the dry-ice/isopropanol bath, allow the mixture to warm to room temperature and then reflux for 2 hours.

Cool the reaction mixture and pour into 10 mL of saturated aqueous $NaHCO_3$ solution. Extract the aqueous mixture with 100 mL of ethyl acetate. Dry the organic layer over anhydrous $MgSO_4$ and concentrate in vacuo to yield 483 mg of a brown oil. Percolate the oil through a flash silica gel column (30 mm × 14 cm) eluting with 5% ethyl acetate in cyclohexane ($R_f$ of the title compound is 0.78) to yield 204 mg (48% yield) of the title compound (a colorless oil).

$^1$H-NMR (300 MHz, $CDCl_3$): δ1.42 (3H,s), 1.60 (15H, s), 1.93–2.14 (20H, m), 4.10 (1H, dtd, J=26, 7.7, 2.6 Hz, CH=$CF_2$), 5.08–5.18 (5H,m).

Mass Spectrum (Chemical Ionization, $CH_4$): 419 $(M+H)^+$ $^{19}$F - NMR (282 MHz, $CDCl_3$, δ from $CFCl_3$): −90.196 (d, J=49 Hz), −92.47 (dd, J=49, 24).

EXAMPLE 3

(E,E,E,E)-1,1,22,22-Tetrafluoro-5,9,14,18-tetramethyl-1,5,9,13,17,21-docosahexaene Prepare lithium diisopropylamide at 0° C. from 1.75 mL of 1.48M n-butyl-lithium (2.6 mmol) in hexane, 0.39 mL (2.8 mmol) of diisopropylamine and 5.5 mL of dry THF.

Cool the mixture in a dry-ice/isopropanol bath and add dropwise difluoromethyl-diphenyl-phosphine oxide (605 mg, 2.4 mmol) in 4 mL THF. After 10 minutes, add 370 mg (1 mmol) of (E,E,E)-4,8,13,17-tetramethyl-4,8,12,16-icosatetraendial (prepared as described by Ceruti et al., *Eur. J. Med. Chem.* 1987, 22, 199–208) in 2 mL of THF over the course of 1 minute. After 1 hour, remove the cooling bath, stir at room temperature for 1 hour and then reflux for 2 hours.

Cool the reaction mixture and pour into 20 mL of saturated aqueous $NaHCO_3$ solution. Extract the aqueous mixture with 100 mL of ethyl acetate and concentrate the organic layer in vacuo to yield an oil. Dissolve the residue in a minimum amount of dichloromethane and percolate the oil through a flash silica gel column (30 mm × 17 cm) eluting with cyclohexane to yield 178 mg (42% yield) of the title compound (a colorless oil).

$^1$H-NMR ($CDCl_3$): δ1.58 (6H,s), 1.59 (6H, s), 1.95–2.05 (20H, m), 4.0 (2H, dtd, J=25.8, 7.7, 2.6), 5.1–5.2 (4H,m).

$^{19}$F - NMR ($CDCl_3$, δ from $CFCl_3$): −90.205 (d, J=48.8), −92.369 (dd, J=25.9, 48.8).

Mass Spectrum (Chemical Ionization, $CH_4$): m/z 427 $(M^+ + H)$.

Analysis: Calculated for $C_{26}H_{38}F_4$: C 73.21, H 8.98; Found: C 73.33, H 9.26.

In a further embodiment, the present invention provides a method of inhibiting squalene epoxidase in a patient in need thereof comprising administering to said patient an effective squalene epoxidase inhibitory amount of a compound of the formula I, II or III. The present invention also provides a method of lowering plasma cholesterol in a patient in need thereof comprising administering to said patient an effective hypocholesterolemic amount of a compound of the formula I, II or III.

As used herein, the term "patient" refers to warm-blooded animals or mammals, including humans. A patient is in need of treatment to inhibit squalene epoxidase or to reduce plasma cholesterol when the patient is suffering from hypercholesterolemia, such as, for example, in the case of a patient suffering from familial hyperlipidemia.

Hypercholesterolemia is a disease state characterized by levels of plasma cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by the use of clinical tests, physical examination and medical/family history, those patients who are suffering from hypercholesterolemia and those who are at risk of developing hypercholesterolemia and thus readily determine if an individual is a patient in need of treatment for hypercholesterolemia.

An effective hypocholesterolemic amount of a compound of formulae I, II or III is an amount which is effective in reducing plasma cholesterol levels or LDL cholesterol levels in a patient in need thereof. As such, successful treatment of a patient for hypercholesterolemia is understood to include reducing a patient's plasma cholesterol or LDL cholesterol levels. Successful treatment for hypercholesterolemia is also understood to include prophylaxis in preventing clinically significant elevations in plasma cholesterol or in LDL cholesterol levels in a patient who is at risk of the development of hypercholesterolemia.

An effective squalene epoxidase inhibitory amount of a compound of formulae I, II or III is an amount which is effective in inhibiting squalene epoxidase in a patient in need thereof which results in the lowering of plasma cholesterol levels or LDL cholesterol levels.

An effective hypocholesterolemic dose or an effective squalene epoxidase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective hypocholesterolemic amount, and an effective squalene epoxidase inhibitory amount, of a compound of the formulae I, II or III will generally vary from about 0.1 milligram per kilogram of body weight per day (mg/kg/day) to about 0.5 grams per kilogram of body weight per day (gm/kg/day). A daily dose of from about 1 mg/kg to about 5 mg/kg is preferred.

In effecting treatment of a patient, compounds of the formulae I, II or III can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Compounds of the formulae I, II or III can be administered in the form of pharmaceutical compositions or medicaments which are made by combining the compounds of the formulae I, II or III with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of the formulae I, II or III may be incorporated with excipients and used in the form of tablets, troches, capsules, elixirs, suspensions, syrups, wafers, chewing gums and the like. These preparations should contain at least 4% of compound of formulae I, II or III, the active ingredient, but may be varied depending upon the particular form and may conveniently be between 4% to about 70% of the weight of the unit. The amount of the active ingredient present in compositions is such that a unit dosage form suitable for administration will be obtained The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of formulae I, II or III may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of formulae I, II and III in their end-use application.

The compounds of formulae I, II and III wherein each optional double bond is present are generally preferred Compounds of formulae I, II and III wherein $R_1$ is $-CH=CF_2$, $-CH=C(CH_3)_2$ or $-CH_2-CH_2OH$ are preferred. Compounds of formulae I, II and III wherein $R_2$ is methyl are preferred.

The following example presents the effect of (E,E,E,E)-1,1-difluoro-5,9,14,18,22-pentamethyl-1,5,9,13,17,21-tricosahexaene on sterol synthesis. The example is understood to be illustrative only and is not intended to limit the scope of the invention in any way. As used in the following examples, the following terms have the meanings indicated: "g" refers to grams, "mg/Kg" refers to milligrams per Kilogram of body weight, "TLC" refers to thin layer chromatography, "dpm" refers to disintegrations per minute, "i.p." refers to intraperitoneal.

EXAMPLE 4

Effect of (E,E,E,E)-1,1-Difluoro-5,9,14,18,22-pentamethyl-1,5,9,13,17,21-tricosahexaene on Sterol Synthesis in the Mouse (E,E,E,E)-1,1-difluoro-5,9,14,18,22-pentamethyl-1,5,9,13,17,21-tricosahexaene was administered orally in peanut oil to groups of six mice in single doses of 2, 7 and 20 mg/Kg. Six hours later $^{14}C$-acetate/$^3H$-mevalonate was injected i.p. and the animals were sacrificed after 30 minutes. Liver nonsaponifiable extracts were prepared and separated by TLC into fractions corresponding to cholesterol, lanosterol, dioxosqualene, oxosqualene and squalene. $^3H$-Radioactivity of the fractions was quantitated by calculating disintegrations per minute. The results are as described in Table 1.

TABLE 1

Effect of (E,E,E,E,E)-1,1-Difluoro-5,9,14,18,22-pentamethyl-1,5,9,13,17,21-tricosahexaene on Sterol Synthesis in the Mouse

| Treatment Group | Cholesterol, dpm/g liver | Lanosterol, dpm/g liver | Dioxo-squalene, dpm/g liver | Oxo-squalene, dpm/g liver | Squalene, dpm/g liver |
|---|---|---|---|---|---|
| Control | 5566 ± 2464 | 1172 ± 210 | 137 ± 91 | 92 ± 46 | 4466 ± 2562 |
| 2 mg/Kg | 1847 ± 2538* | 463 ± 396* | 208 ± 105 | 62 ± 28 | 9656 ± 6305 |
| 7 mg/Kg | 1241 ± 1243* | 362 ± 187* | 156 ± 75 | 56 ± 25 | 12183 ± 5974* |
| 20 mg/Kg | 359 ± 161* | 248 ± 94* | 226 ± 53* | 72 ± 33 | 19152 ± 2753* |

*Significantly different from control value

These results demonstrate a significant inhibition of sterol synthesis by (E,E,E,E)-1,1-difluoro-5,9,14,18,22-pentamethyl-1,5,9,13,17,21-tricosahexaene in the mouse which is consistant with an inhibition of squalene epoxidase.

What is claimed is:

1. A compound of the formula

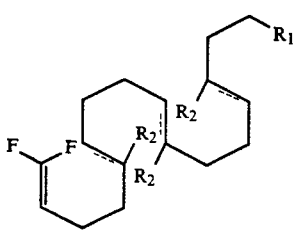

wherein
each dotted line individually represents an optional double bond,
$R_1$ is $-CH=CF_2$, $-CH=CR_3R_4$ or $-R_5-OH$, wherein $R_3$ and $R_4$ are each independently a $C_1-C_4$ alkyl, and $R_5$ is a $C_1-C_4$ alkylene, and
each $R_2$ is independently hydrogen or methyl.

2. A compound of the formula

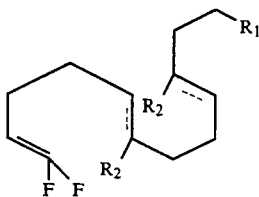

wherein
each dotted line individually represents an optional double bond,
$R_1$ is $-CH=CF_2$, $-CH=CR_3R_4$ or $-R_5-OH$, wherein $R_3$ and $R_4$ are each independently a $C_1-C_4$ alkyl, and $R_5$ is a $C_1-C_4$ alkylene, and
each $R_2$ is independently hydrogen or methyl.

3. A method of lowering plasma cholesterol in a patient in need thereof comprising administering to said patient an effective hypocholesterolemic amount of a compound of claim 1 or 2.

4. A method of inhibiting squalene epoxidase in a patient in need thereof comprising administering to said patient an effective squalene epoxidase inhibitory amount of a compound of claim 1 or 2.

5. A composition comprising a compound of claim 1 or 2 in admixture of otherwise in association with an inert carrier.

6. A pharmaceutical composition comprising an effective hypocholesterolemic amount of a compound of claim 1 or 2 in admixture or otherwise in association with one or more pharmaceutically acceptable carriers or excipients.

* * * * *